United States Patent
Boiteau et al.

(10) Patent No.: US 9,408,793 B2
(45) Date of Patent: Aug. 9, 2016

(54) SELECTIVE COMPOUNDS INHIBITING CYP26A1 USEFUL IN COSMETIC AND PHARMACEUTICAL COMPOSITIONS

(71) Applicant: GALDERMA RESEARCH & DEVELOPMENT, Biot (FR)

(72) Inventors: Jean-Guy Boiteau, Valbonne (FR); Michel Rivier, Nice (FR); Gérard Feraille, Mougins (FR); André Jomard, Saint Vallier de Thiey (FR)

(73) Assignee: GALDERMA RESEARCH & DEVELOPMENT, Biot (FR)

( * ) Notice: Subject to any disclaimer, the term of this patent is extended or adjusted under 35 U.S.C. 154(b) by 0 days.

(21) Appl. No.: 14/417,035

(22) PCT Filed: Jul. 23, 2013

(86) PCT No.: PCT/FR2013/051769
§ 371 (c)(1),
(2) Date: Jan. 23, 2015

(87) PCT Pub. No.: WO2014/016507
PCT Pub. Date: Jan. 30, 2014

(65) Prior Publication Data
US 2015/0190323 A1   Jul. 9, 2015

(30) Foreign Application Priority Data

Jul. 23, 2012 (FR) ..................... 12 57128

(51) Int. Cl.
A61K 8/46 (2006.01)
A61Q 19/08 (2006.01)
C07C 317/44 (2006.01)
A61Q 19/02 (2006.01)
A61Q 19/04 (2006.01)
A61Q 19/00 (2006.01)

(52) U.S. Cl.
CPC . A61K 8/46 (2013.01); A61Q 19/00 (2013.01); A61Q 19/02 (2013.01); A61Q 19/04 (2013.01); A61Q 19/08 (2013.01); C07C 317/44 (2013.01); C07C 2102/10 (2013.01)

(58) Field of Classification Search
CPC ......... A61K 8/46; A61Q 19/00; A61Q 19/02; A61Q 19/04; A61Q 19/08; C07C 317/44; C07C 2102/10
See application file for complete search history.

(56) References Cited

U.S. PATENT DOCUMENTS 5,087,743 A * 2/1992 Janssen .................... A61K 8/33
558/411

FOREIGN PATENT DOCUMENTS

WO   99/10322 A1   3/1999

OTHER PUBLICATIONS

English Translation of International Search Report dated Sep. 2, 2013 corresponding to International Patent Application No. PCT/FR2013/051769, 3 pages.
Njar, V.C.O., et al., "Retinoic acid metabolism blocking agents (RAMBAs) for treatment of cancer and dermatological diseases," Bioorganic & Medicinal Chemistry, Pergamon, GB, vol. 14, No. 13, Jul. 2006, pp. 4323-4340.
Kuo-Long, Y, et al., "Structural modifications of 6-naphthalene-2-carboxylate retinoids," Bioorganic & Medicinal Chemistry Letters, Pergamon, GB, vol. 6, No. 23, Dec. 1996, pp. 2865-2870.

* cited by examiner

*Primary Examiner* — Shailendra Kumar
(74) *Attorney, Agent, or Firm* — Dentons US LLP

(57) ABSTRACT

Compounds or salts thereof are described that correspond to general formula (I) below:

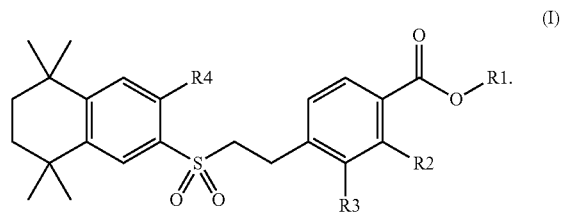

Also described, are pharmaceutical and cosmetic compositions that include these compounds. Methods of using these compounds and compositions for the treatment of pathological conditions are also described.

18 Claims, 1 Drawing Sheet

SELECTIVE COMPOUNDS INHIBITING CYP26A1 USEFUL IN COSMETIC AND PHARMACEUTICAL COMPOSITIONS

CROSS-REFERENCE TO PRIOR APPLICATIONS

This application is a National Stage of PCT/FR2013/051769, filed Jul. 23, 2013, and designating the United States (published on Jan. 30, 2014, as WO 2014/16507 A1), which claims priority under 35 U.S.C. §119 to French Patent Application No. 1257128, filed Jul. 23, 2012, each hereby expressly incorporated by reference in its entirety and each assigned to the assignee hereof.

The present invention relates to novel compounds, to the pharmaceutical compositions containing these compounds and also to the use of these compounds and of these compositions for the treatment of pathological conditions. It also relates to the cosmetic uses of the novel compounds.

The present invention relates to novel compounds which are selective CYP26A1 inhibitors, to the use thereof and to the synthesis thereof.

Vitamin A and its derivatives, retinoids, are involved in various biological processes, such as cell proliferation, differentiation and apoptosis.

Natural and synthetic retinoids are conventionally used in the treatment of pathological skin conditions such as acne, psoriasis and ichthyosis (Van de Kerkhof PC. Dermatol. Ther. 2006; 19:252-63). However, these active agents can also cause a large variety of adverse effects, such as skin irritation (Mills C M, Marks R. Drug Saf 1993; 9:280-90.), which led researchers to turn their investigations towards novel medicaments, which have the same positive effects as retinoids but without their side effects.

Another objective of researchers was to target the desired pharmacological effect at the level of tissues where vitamin A is metabolized.

Retinoic acid (RA), which is the active metabolite of vitamin A, exists in 4 isomeric forms, all-trans retinoic acid (atRA), 13-cis-retinoic acid (13cisRA), 9-cis-retinoic acid (9cisRA) and 9,13-di-cis-retinoic acid.

After the distribution of vitamin A in the skin by serum retinol-binding protein, the keratinocytes either store the vitamin in the form of retinol esters, by means of a reaction catalysed by the lecithin retinol acyltransferase (LRAT) enzyme, or metabolize it to atRA by means of a two-step reaction, in which it is irreversibly catalysed by retinal dehydrogenase-2 (RALDH2; ALDH1A2) (Roos T C, Jugert F K, Merk H F et al. Pharmacol Rev 1998; 50:315-33). atRA is biologically the most active metabolite and binds to specific nuclear transcription factors, such as retinoic acid receptors (RARs), which regulate the expression of numerous genes.

The cellular degradation of atRA is regulated by a family of cytochrome P450 (CYP)-dependent microsomal enzymes, including CYP26. The CYP26 family is composed of three isoforms CYP26A1, CYP26B1 and CYP26C1 (Abu-Abed S S, Beckett B R , Chiba H et al. J Biol Chem 1998; 273:2409-15; Sonneveld E, van den Brink C E, van der Leede B M et al. Cell Growth Differ 1998; 9:62937; Ray W J, Bain G, Yao M et al. J Biol Chem 1997; 272:18702-8; Taimi M, Helvig C, Wisniewski J et al. J Biol Chem 2004; 279:77-85). The CYP26A1 and CYP26B1 isoforms oxidize atRA to 4-hydroxyretinoic acid and to 4-oxo-retinoic acid, which are much less active (Duell E A, Astrom A, Griffiths C E et al. J Clin Invest 1992; 90:1269-74). The final isoform, CYP26C1, appears to play a substantially different metabolic role since it is capable of metabolizing both atRA but also 9-cis retinoic acid (Helvig C, Taimi M, Cameron D, Jones G, Petkovich M. J Pharmacol Toxicol Methods. 2011 November-December; 64(3):258-63). All these CYP26 enzymes can be induced by exogenous atRA, causing the induction of its degradation (Loudig 0, Babichuk C, White J et al. Mol Endocrinol 2000; 14:1483-97). The studies on animals in which the gene encoding CYP26A1, CYP26B1 or CYP26C1 had been inactivated (Knock-out or KO mice) show that CYP26A1 and CYP26B1 are essential proteins (Thatcher J E, Isoherranen N. Expert Opin Drug Metab Toxicol. 2009 August; 5(8):875-86). Indeed, the Cyp26a1−/− and C 26b1−/− phenotypes (i.e. homozygous phenotypes not expressing the CYP26a1 or b 1 gene) are lethal. The animals produced by homologous recombination are not viable, contrary to the Cyp26c1−/− phenotype, which itself does not show any impairment in terms of embryonic development or at birth. The fact that the CYP26a1 and b 1 KO animals are not viable underlines the respective importance of these 2 proteins and the fact that they are not redundant from a functional point of view: indeed, the loss of CYP26A1 is not compensated for by CYP26B1 and vice versa. Consequently, they have very different roles and must be considered as distinct entities. mRNA and protein expression studies for these 2 CYP26s have demonstrated quite similar expression profiles with, however, marked differences for certain organs (Topletz A R, Thatcher J E, Zelter A, Lutz J D, Tay S, Nelson W L, Isoherranen N. Biochem Pharmacol. 2012 January 1; 83(1):149-63). For example, the mRNA of the CYP26A1 isoform is strongly expressed in the liver in humans, whereas the CYP26B1 isoform is virtually absent therein. The mRNA of the CYP26A1 isoform is, on the contrary, not detected in the bladder, the colon and the ileum, whereas the mRNA of CYP26B 1 is present therein. Conversely, CYP26B 1 is very strongly expressed in the cerebellum, whereas the CYP26A1 isoform is not detected therein. These differences observed at the mRNA level are also partly found at the protein level and, generally, it appears that the CYP26B1 isoform is expressed quite ubiquitously, whereas the CYP26A1 isoform has a more restricted expression profile (Topletz A R, Thatcher J E, Zelter A, Lutz J D, Tay S, Nelson W L, Isoherranen N. Biochem Pharmacol. 2012 Jan 1; 83(1):149-63). Given the fact that CYP26B1 is expressed in a large number of tissues and that its biological activity appears to be distinct from that of CYP26A1, it clearly appears that inhibitors specific for the CYP26A1 subtype will have the major advantage of blocking the metabolic pathways of atRA only in a limited number of tissues, in particular the skin. The consequence of this would be to limit the adverse effects potentially mediated by the CYP26B1 isoform and therefore to improve the safety of patients able to be treated with inhibitors of this type.

Thus, by selectively inhibiting CYP26A1 activity, it should be possible to increase the endogenous level of atRA in the skin. It has been demonstrated that the enzymatic activity of CYP26A1 is much higher than that of CYP26B1. Indeed, the atRA-depleting enzymatic activity of CYP26A1 is about 20 times that of CYP26B1. In the skin, since the 2 isoforms are expressed in the same way at the protein level, it is therefore reasonable to consider that the CYP26A1 isoform is predominantly responsible for the elimination of atRA (Topletz A R, Thatcher J E, Zelter A, Lutz J D, Tay S, Nelson W L, Isoherranen N. Biochem Pharmacol. 2012 Jan. 1; 83(1):149-63). This would not, on the other hand, be the case in the tissues where CYP26A1 is not expressed and where the atRA-eliminating activity is provided by CYP26B1, such as the cerebellum.

A CYP26A1-specific endogenous RA metabolism inhibitor could have a beneficial effect on cell growth and differentiation, in particular that of epithelial cells such as keratinocytes.

Generally, these inhibitors are called retinoic acid metabolism blocking agents or RAMBAs. More particularly, novel compounds which are specific inhibitors of CYP26A1 should be called "CYP26A1-specific RAMBAs". This type of totally specific inhibitor has never been described to date and constitutes an important pharmacological and medical asset.

Nevertheless, a certain number of non-specific RAMBA (retinoic acid metabolism blocking agent) compounds are already known (Njar, V. C. O., et al., J. Bioorg. Med. Chem., 14, 4323 (2006)). They have been described in the treatment of disorders associated with a disfunction of epithelial cells (for instance those of the epidermis) and disorders associated with an abnormal atRA concentration in certain tissues.

The first RAMBA molecule which was discovered as being effective in the treatment of psoriasis and ichthyosis is Liarozole (Kang et al. J Inv Dermatol, 104 (2) August 1996, 183-187). Liarozole has a weak enzymatic specificity and can therefore inhibit other pathways mediated by CYP enzymes, like for instance the biosynthesis of adrenal hormone. This can generate unwanted side effects attributed to a lack of CYP isoform specificity. Moreover, it is extremely complex to manage all the drug interactions that may occur with compounds of this type, given the broad spectrum of CYPs inhibited. These two drawbacks (numerous potential adverse effects and numerous drug interactions) greatly limit the potential use of this type of compound, especially in polymedicated patients.

Rambazole® (or Talarozole) is a second-generation CYP26 inhibitor which is more selective compared with this activity on the other cytochromes, such as CYP3A4 and CYP2C8 (Geria & Scheinfeld Curr. Opinion Invest. Drugs, 2008 9(11) : 12228-1237). Nevertheless, if only the CYP26s are considered, this compound has a relatively low selectivity for CYP26A1, with an activity of about 62 nM on the CYP26B1 isoform. In order to guarantee good specificity of blocking of one isoform with respect to another, it is necessary for the inhibition ratio to be at least 100.

Thus, there remains a constant need to develop compounds which are used in cosmetic and pharmaceutical compositions and which exhibit an improved biological activity as CYP26 inhibitors, in particular CYP26A1 inhibitors.

SUMMARY OF THE INVENTION

The Applicant has discovered CYP26 inhibitors according to the invention which act as retinoic acid metabolism blocking agents (RAMBAs). The compounds possess an improved biological activity as CYP26 inhibitors which have a great selectivity for CYP26A1 compared with CYP26B1. This increased selectivity makes it possible to expect a considerable efficacy in the organs where CYP26A1 is well expressed, such as the skin, while at the same time guaranteeing that the CYP26B 1-mediated "outside target" pharmacological adverse effects will be very limited, or even nonexistent. The expected benefit/risk ratio is therefore much more favourable for this type of inhibitor which can guarantee a level of selectivity greater than 100 between the 2 enzymes.

The present invention relates to novel compounds or a salt thereof corresponding to general formula (I) below:

(I)

in which:
R1 represents a hydrogen atom or a $C_1$-$C_3$ alkyl;
R2 represents a hydrogen, a $C_1$-$C_3$ alkyl, a fluorine, or a $CF_3$ radical;
R3 represents a hydrogen, a $C_1$-$C_3$ alkyl, a fluorine, or a $CF_3$ radical; and
R4 represents a hydrogen, a $C_1$-$C_3$ alkyl, or a $CF_3$ radical.

Preferably, R1 is selected from the group consisting of a hydrogen, a methyl and an ethyl, preferably a hydrogen; R2 is selected from the group consisting of a hydrogen, a methyl, a fluorine, or a $CF_3$ radical; R3 is selected from the group consisting of a hydrogen, a methyl, a fluorine, or a $CF_3$ radical; and R4 is selected from the group consisting of a hydrogen, a methyl and a $CF_3$ radical.

The preferred compounds of formula (I) according to the present invention are chosen from:
4-[2-(5,5,8,8-tetramethyl-5,6,7,8-tetrahydronaphthalene-2-sulphonyl)ethyl]benzoic acid;
4-[2-(5,5,8,8-tetramethyl-5,6,7,8-tetrahydronaphthalene-2-sulphonyl)ethyl]-3-trifluoromethylbenzoic acid;
4-[2-(3,5,5,8,8-pentamethyl-5,6,7,8-tetrahydronaphthalene-2-sulphonyl)ethyl]-3-trifluoromethylbenzoic acid;
methyl 4-[2-(5,5,8,8-tetramethyl-5,6,7,8-tetrahydronaphthalene-2-sulphonyl)ethyl]benzoate;
ethyl 4-[2-(5,5,8,8-tetramethyl-5,6,7,8-tetrahydronaphthalene-2-sulphonyl)ethyl]benzoate;
methyl 4-[2-(5,5,8,8-tetramethyl-5,6,7,8-tetrahydronaphthalene-2-sulphonyl)ethyl]-3-trifluoromethyl benzoate;
ethyl 4-[2-(5,5,8,8-tetramethyl-5,6,7,8-tetrahydronaphthalene-2-sulphonyl)ethyl]-3-trifluoromethyl benzoate;
2-methyl-4-[2-(5,5,8,8-tetramethyl-5,6,7,8-tetrahydronaphthalene-2-sulphonyl)ethyl]benzoic acid;
2-fluoro-4-[2-(5,5,8,8-tetramethyl-5,6,7,8-tetrahydronaphthalene-2-sulphonyl)ethyl]benzoic acid;
4-[2-(5,5,8,8-tetramethyl-5,6,7,8-tetrahydronaphthalene-2-sulphonyl)ethyl]-2-trifluoromethyl benzoic acid;
3-methyl-4-[2-(5,5,8,8-tetramethyl-5,6,7,8-tetrahydronaphthalene-2-sulphonyl)ethyl]benzoic acid;
3-fluoro-4-[2-(5,5,8,8-tetramethyl-5,6,7,8-tetrahydronaphthalene-2-sulphonyl)ethyl]benzoic acid;
4-[2-(5,5,8,8-tetramethyl-3-trifluoromethyl-5,6,7,8-tetrahydronaphthalene-2-sulphonyl)ethyl]benzoic acid;
3-methyl-4-[2-(3,5,5,8,8-pentamethyl-5,6,7,8-tetrahydronaphthalene-2-sulphonyl)ethyl]benzoic acid;
2-methyl-4-[2-(3,5,5,8,8-pentamethyl-5,6,7,8-tetrahydronaphthalene-2-sulphonyl)ethyl]benzoic acid;
2,3-dimethyl-4-[2-(5,5,8,8-tetramethyl-5,6,7,8-tetrahydronaphthalene-2-sulphonyl)ethyl]benzoic acid;
2,3-difluoro-4-[2-(5,5,8,8-tetramethyl-5,6,7,8-tetrahydronaphthalene-2-sulphonyl)ethyl]benzoic acid; and
methyl 2-methyl-4-[2-(3,5,5,8,8-pentamethyl-5,6,7,8-tetrahydronaphthalene-2-sulphonyl)ethyl]benzoate.

Preferentially, the compounds of formula (I) are chosen from the group consisting of:
4-[2-(5,5,8,8-tetramethyl-5,6,7,8-tetrahydronaphthalene-2-sulphonyl)ethyl]benzoic acid;

4-[2-(5,5,8,8-tetramethyl-5,6,7,8-tetrahydronaphthalene-2-sulphonyl)ethyl]-3-trifluoromethylbenzoic acid;

4-[2-(3,5,5,8,8-pentamethyl-5,6,7,8-tetrahydronaphthalene-2-sulphonyl)ethyl]-3-trifluoromethylbenzoic acid; and even more preferably the compound of formula (I) is 4-[2-(5,5,8,8-tetramethyl-5,6,7,8-tetrahydronaphthalene-2-sulphonyl)ethyl]benzoic acid.

The present invention also relates to a composition comprising a compound of formula (I) in combination with a solvent or a support. Preferably, the composition is a pharmaceutical or cosmetic composition and the solvent or support is dermatologically acceptable.

A compound or the composition of the invention can be used as a medicament, particularly for preventing or treating the following pathological conditions:

1) dermatological conditions associated with a keratinization disorder relating to cell differentiation and proliferation, in particular for treating common acne, comedonal acne, polymorphic acne, acne rosacea, nodulocystic acne, acne conglobata, senile acne, secondary acne such as solar acne, acne medicamentosa or occupational acne;
2) keratinization disorders, in particular ichthyosis, ichthyosiform conditions, lamellar ichthyosis, Darier's disease, palmoplantar keratodermia, leukoplakia, pityriasis rubra pilaris and leucoplasiform conditions, cutaneous or mucosal (buccal) lichen;
3) dermatological conditions with an inflammatory immunoallergic component, with or without a cell proliferation disorder, and in particular all forms of psoriasis, whether cutaneous, mucosal or ungueal, and even psoriatic arthritis, or else atopic dermatitis and the various forms of eczema;
4) skin disorders caused by exposure to UV radiation for reducing actinic keratoses and pigmentations, or any pathological conditions associated with chronological or actinic ageing, such as xerosis, lentigines or lentigo;
5) any condition associated with benign dermal or epidermal proliferations, whether or not they are of viral origin, such as common warts, flat warts, molluscum contagiosum and epidermodysplasia verruciformis, or oral or floride papillomatoses;
6) dermatological disorders such as immune dermatoses, for instance lupus erythematosus, bullous immune diseases and collagen diseases, such as sclerodermia;
7) stigmata of epidermal and/or dermal atrophy induced by local or systemic corticosteroids, or any other form of cutaneous atrophy;
8) healing disorders, or for preventing or repairing stretch marks, or else for promoting healing;
9) conditions of fungal origin at the cutaneous level, such as tinea pedis and tinea versicolor;
10) pigmentation disorders, such as hyperpigmentation, melasma, hypopigmentation or vitiligo;
11) cutaneous or mucosal cancerous or precancerous conditions, such as actinic keratoses, Bowen's disease, in-situ carcinomas, keratoacanthoma and skin cancers such as basal cell carcinoma (BCC), squamous cell carcinoma (SCC) and cutaneous lymphomas such as T lymphoma, acute promyelocytic leukaemia, neuroblastomas, acute myeloid leukaemias, prostate cancer and breast cancer.

Preferably, the compound or the composition as defined above is used for the treatment of dermatological diseases such as acne, ichthyosis, ichthyosiform conditions, palmoplantar hyperkeratosis or psoriasis.

The compound or the composition of the invention is also used for the treatment of skin ageing. Preferably, the present invention relates quite particularly to the use for the treatment of cutaneous atrophy, of pigmentation spots, of wrinkles or fine lines, of skin dryness, of skin roughness, of solar elastosis and of telangiectasia.

The present invention also relates to the cosmetic use of a compound or a composition according to the invention for treating or preventing pigmentation spots, for reducing skin pigmentation, for treating or preventing cutaneous atrophy, for treating or preventing skin ageing, in particular wrinkles and/or fine lines, for treating or preventing the effects of any physical or chemical agent causing an acceleration of skin ageing, for improving the elasticity and/or the tonicity of the skin and/or for firming the skin.

DETAILED DESCRIPTION OF THE INVENTION

Figure 1:
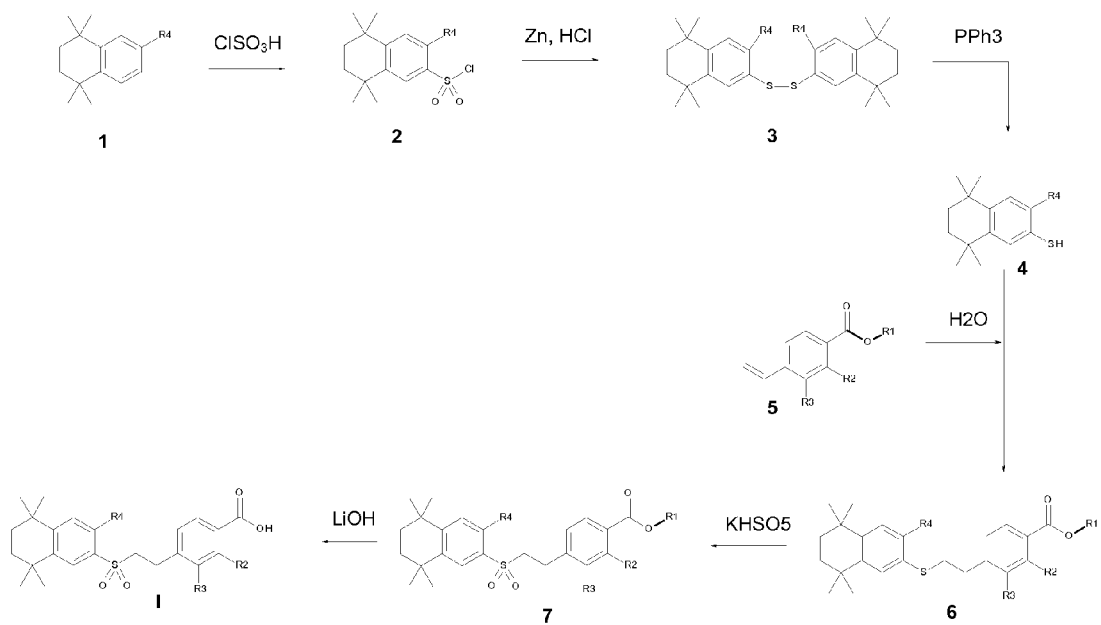
FIG. 1: General synthesis scheme for the compounds of the invention. In one particular mode, R1 is a methyl.

The inventors have discovered and identified novel compounds which have a CYP26 inhibitor effect and which also exhibit great selectivity for CYP26A1 compared with CYP26B1. These compounds can be used in pharmaceutical and cosmetic compositions, alone or in combination with other compounds, in particular a compound of the vitamin A family, in order to promote effects which are beneficial to the health and to esthetics.

The present invention therefore relates to novel compounds or a salt thereof corresponding to general formula (I) below:

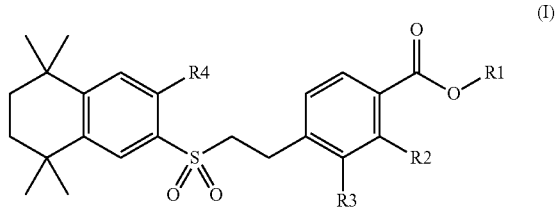

(I)

in which:

R1 represents a hydrogen atom or a $C_1$-$C_3$ alkyl;

R2 represents a hydrogen, a $C_1$-$C_3$ alkyl, a fluorine, or a $CF_3$ radical;

R3 represents a hydrogen, a $C_1$-$C_3$ alkyl, a fluorine, or a $CF_3$ radical; and R4 represents a hydrogen, a $C_1$-$C_3$ alkyl, or a $CF_3$ radical.

In a first preferential embodiment, R1 is selected from the group consisting of a hydrogen, a methyl and an ethyl. In particular, R1 is a hydrogen.

In a second preferential embodiment, R2 is selected from the group consisting of a hydrogen, a methyl, a fluorine, or a $CF_3$ radical.

In a third preferential embodiment, R3 is selected from the group consisting of a hydrogen, a methyl, a fluorine, or a $CF_3$ radical.

In a fourth preferential embodiment, R4 is selected from the group consisting of a hydrogen, a methyl and a $CF_3$ radical.

Preferably, R1 is selected from the group consisting of a hydrogen, a methyl and an ethyl;

R2 and R3, independently of one another, are selected from the group consisting of a hydrogen, a methyl, a fluorine, or a $CF_3$ radical; and R4 is selected from the group consisting of a hydrogen, a methyl and a $CF_3$ radical.

In one particular embodiment, R1 is selected from the group consisting of a hydrogen and a $C_1$-$C_3$ alkyl, preferably a methyl and an ethyl; and R2, R3 and R4 are hydrogens.

Unless otherwise indicated, the following definitions apply to the whole of the description and the claims.

The term "alkyl" denotes a linear or branched, saturated hydrocarbon-based chain of which the number of carbon atoms is specified.

The preferred alkyl groups contain from 1 to 3 carbon atoms in the chain. They comprise methyl, ethyl and propyl, in particular isopropyl.

By way of example of compounds corresponding to general formula (I), mention may be made of the following compounds, without this list being limiting:
4-[2-(5,5,8,8-tetramethyl-5,6,7,8-tetrahydronaphthalene-2-sulphonyl)ethyl]benzoic acid;
4-[2-(5,5,8,8-tetramethyl-5,6,7,8-tetrahydronaphthalene-2-sulphonyl)ethyl]-3-trifluoromethylbenzoic acid;
4-[2-(3,5,5,8,8-pentamethyl-5,6,7,8-tetrahydronaphthalene-2-sulphonyl)ethyl]-3-trifluoromethylbenzoic acid;
methyl 4-[2-(5,5,8,8-tetramethyl-5,6,7,8-tetrahydronaphthalene-2-sulphonyl)ethyl]benzoate;
ethyl 4-[2-(5,5,8,8-tetramethyl-5,6,7,8-tetrahydronaphthalene-2-sulphonyl)ethyl]benzoate;
methyl 4-[2-(5,5,8,8-tetramethyl-5,6,7,8-tetrahydronaphthalene-2-sulphonyl)ethyl]-3-trifluoromethyl benzoate;
ethyl 4-[2-(5,5,8,8-tetramethyl-5,6,7,8-tetrahydronaphthalene-2-sulphonyl)ethyl]-3-trifluoromethyl benzoate;
2-methyl-4-[2-(5,5,8,8-tetramethyl-5,6,7,8-tetrahydronaphthalene-2-sulphonyl)ethyl]benzoic acid;
2-fluoro-4-[2-(5,5,8,8-tetramethyl-5,6,7,8-tetrahydronaphthalene-2-sulphonyl)ethyl]benzoic acid;
4-[2-(5,5,8,8-tetramethyl-5,6,7,8-tetrahydronaphthalene-2-sulphonyl)ethyl]-2-trifluoromethyl benzoic acid;
3-methyl-4-[2-(5,5,8,8-tetramethyl-5,6,7,8-tetrahydronaphthalene-2-sulphonyl)ethyl]benzoic acid;
3-fluoro-4-[2-(5,5,8,8-tetramethyl-5,6,7,8-tetrahydronaphthalene-2-sulphonyl)ethyl]benzoic acid;
4-[2-(5,5,8,8-tetramethyl-3-trifluoromethyl-5,6,7,8-tetrahydronaphthalene-2-sulphonyl)ethyl]benzoic acid;
3-methyl-4-[2-(3,5,5,8,8-pentamethyl-5,6,7,8-tetrahydronaphthalene-2-sulphonyl)ethyl]benzoic acid;
2-methyl-4-[2-(3,5,5,8,8-pentamethyl-5,6,7,8-tetrahydronaphthalene-2-sulphonyl)ethyl]benzoic acid;
2,3-dimethyl-4-[2-(5,5,8,8-tetramethyl-5,6,7,8-tetrahydronaphthalene-2-sulphonyl)ethyl]benzoic acid;
2,3-difluoro-4-[2-(5,5,8,8-tetramethyl-5,6,7,8-tetrahydronaphthalene-2-sulphonyl)ethyl]benzoic acid; and
methyl 2-methyl-4-[2-(3,5,5,8,8-pentamethyl-5,6,7,8-tetrahydronaphthalene-2-sulphonyl)ethyl]benzoate.

Preferably, the compound of general formula (I) is chosen from the group consisting of
4-[2-(5,5,8,8-tetramethyl-5,6,7,8-tetrahydronaphthalene-2-sulphonyl)ethyl]benzoic acid;
4-[2-(5,5,8,8-tetramethyl-5,6,7,8-tetrahydronaphthalene-2-sulphonyl)ethyl]-3-trifluoromethylbenzoic acid;
4-[2-(3,5,5,8,8-pentamethyl-5,6,7,8-tetrahydronaphthalene-2-sulphonyl)ethyl]-3-trifluoromethylbenzoic acid.

A preferred compound according to the invention is 4-[2-(5,5,8,8-tetramethyl-5,6,7,8-tetrahydronaphthalene-2-sulphonyl)ethyl]benzoic acid.

The present invention relates to a composition comprising a compound corresponding to general formula (I) or a salt thereof as defined above, in combination with a solvent or a support.

In particular, the composition is a cosmetic composition and the solvent or support is dermatologically acceptable. Thus, the composition comprises a cosmetically effective amount of the compound, i.e. an amount sufficient to enable a cosmetic effect.

The present invention also relates to a pharmaceutical composition comprising an effective amount of a compound corresponding to general formula (I) or of a pharmaceutically acceptable salt of said compound as described above, in combination with a pharmaceutically acceptable, preferably dermatologically acceptable, solvent or support. Thus, the composition comprises a therapeutically effective amount of the compound, i.e. an amount sufficient to enable a therapeutic or pharmaceutical effect.

The compounds of the invention in the form of salts, in particular in the form of dermatologically, pharmaceutically or cosmetically acceptable salts, include in particular the acid addition salts, the basic addition salts, the metal salts, and the ammonium or alkyl ammonium salts, in particular those which are pharmaceutically or cosmetically acceptable. The acid addition salts include the inorganic salts and the organic salts. Representative examples of suitable inorganic acids comprise hydrochloric acid, hydrobromic acid, iodic acid, phosphoric acid, etc. Representative examples of suitable organic acids comprise acetic acid, formic acid, propionic acid, benzoic acid, maleic acid, fumaric acid, succinic acid, tartaric acid, citric acid, trichloroacetic acid, trifluoroacetic acid, etc. Other examples of organic or inorganic acid addition salts are provided in J. Pharm. Sci., 1977, 66, 2 and in the "Handbook of Pharmaceutical Salts: Properties, Selection and Use" edited by P. Heinrich Stahl and Camille G. Wermuth, 2002. Examples of metal salts include the lithium salts, sodium salts, potassium salts or magnesium salts, etc. Examples of ammonium and alkyl ammonium salts include the ammonium, methylammonium, dimethylammonium, trimethylammonium, ethylammonium, hydroxyethylammonium, diethylammonium, butylammonium, tetramethylammonium, etc., salts. Examples of organic bases include lysine, arginine, guanidine, diethanolamineoline, etc.

The present invention relates to a compound or a pharmaceutical composition as described above, for use as a medicament. It also relates to the use of a compound or a composition according to the present application, for preparing a medicament. Finally, it relates to treatment methods comprising the administration of an effective amount of a compound or of a composition according to the present application.

The present invention thus relates to the compounds according to the invention, or a composition comprising at least one compound according to the invention, or a pharmaceutically acceptable salt thereof, for use for treating the following pathological conditions:
1) dermatological conditions associated with a keratinization disorder relating to cell differentiation and proliferation, in particular for treating common acne, comedonal acne, polymorphic acne, acne rosacea, nodulocystic acne, acne conglobata, senile acne, secondary acne such as solar acne, acne medicamentosa or occupational acne;
2) keratinization disorders, in particular ichthyosis, ichthyosiform conditions, lamellar ichthyosis, Darier's disease, palmoplantar keratodermia, leukoplakia, pityriasis rubra pilaris and leucoplasiform conditions, cutaneous or mucosal (buccal) lichen;

3) dermatological conditions with an inflammatory immunoallergic component, with or without a cell proliferation disorder, and in particular all forms of psoriasis, whether cutaneous, mucosal or ungueal, and even psoriatic arthritis, or else atopic dermatitis and the various forms of eczema;
4) skin disorders caused by exposure to UV radiation for reducing actinic keratoses and pigmentations, or any pathological conditions associated with chronological or actinic ageing, such as xerosis, lentigines or lentigo;
5) any condition associated with benign dermal or epidermal proliferations, whether or not they are of viral origin, such as common warts, flat warts, molluscum contagiosum and epidermodysplasia verruciformis, or oral or floride papillomatoses;
6) dermatological disorders such as immune dermatoses, for instance lupus erythematosus, bullous immune diseases and collagen diseases, such as sclerodermia;
7) stigmata of epidermal and/or dermal atrophy induced by local or systemic corticosteroids, or any other form of cutaneous atrophy;
8) healing disorders, or for preventing or repairing stretch marks, or else for promoting healing;
9) conditions of fungal origin at the cutaneous level, such as tinea pedis and tinea versicolor;
10) pigmentation disorders, such as hyperpigmentation, melasma, hypopigmentation or vitiligo;
11) cutaneous or mucosal cancerous or precancerous conditions, such as actinic keratoses, Bowen's disease, in-situ carcinomas, keratoacanthoma and skin cancers such as basal cell carcinoma (BCC), squamous cell carcinoma (SCC) and cutaneous lymphomas such as T lymphoma, acute promyelocytic leukaemia, neuroblastomas, acute myeloid leukaemias, prostate cancer and breast cancer.

In one preferred embodiment according to the invention, the compound or the pharmaceutical composition is used in the treatment of dermatological diseases such as acne, ichthyosis, ichthyosiform conditions, palmoplantar hyperkeratosis or psoriasis.

The present invention also relates to the use of a compound or a composition according to the invention, for treating skin ageing.

The term "skin ageing" is intended to mean chronological and/or actinic ageing, where the epidermis undergoes numerous modifications or degradations which, with age, result in a modification of the microrelief, the appearance of wrinkles and fine lines, a modification of the mechanical properties of the skin with a decrease in firmness and in elasticity and a loss of radiance of the complexion. At the tissue level, the ageing manifests itself through a disorganization of the epidermal architecture, of the dermal-epidermal junction and of the dermis, and also of the blood irrigation and innervation systems, a slowing of various metabolisms, such as those involved in the equilibrium of the barrier function. At the cell level, the ageing results in a modification of the physiology or of the metabolism of the main cell types of the dermis (fibroblasts) and of the epidermis (keratinocytes). Chronological ageing or ageing associated with exposure to the sun (photoageing) or to a physical or chemical agent can be accompanied by pigmentation spots, by cutaneous atrophy, by wrinkles or fine lines, by skin dryness, by skin roughness, by solar elastosis, but also by telangiectasia which is small dilated vessels at the surface of the skin. More generally and non-exhaustively, this ageing associated with age or with exposure to the sun or to a physical or chemical agent is responsible for a loss of elasticity, suppleness and tonicity of the skin through the modification of the support proteins of the dermis, such as collagens, and modifications of physiological and biophysical parameters such as the moisturization of the skin or its barrier properties. This skin ageing also results in a general modification of the appearance of the skin, of its colour, fineness, grain and softness. These various skin properties can be beneficially modified by treatment with the compounds and compositions of the invention.

The present invention therefore particularly relates to the cosmetic use of a compound or of a composition according to the invention, for maintaining and/or stimulating the moisturization of the skin, for treating dry skin or for treating or preventing ageing of the skin or of the skin appendages and/or photoageing, in particular for treating or preventing pigmentation spots, wrinkles, in particular deep wrinkles and/or fine lines, for reducing ptosis, or improving the quality and/or the transparency of the skin, for improving or restoring the suppleness, the elasticity and/or the tonicity of the skin, and for firming the skin.

The amount of compounds according to the invention used in the compositions of the invention depends on the cosmetic or therapeutic effect and can therefore vary. A concentration range of the compound of the invention may be comprised between approximately 0.001 g/l or g/kg and approximately 1000 g/l or g/kg of composition, and preferably comprised between approximately 0.1 g/l or g/kg and approximately 10 g/l or g/kg of composition appears to be suitable for the compositions of the invention.

The compositions according to the invention comprise a dose ranging from 0.000001% to 10%, preferentially from 0.001% to 5% and even more preferentially from 0.1% to 3% by total weight of a compound of the invention relative to the total weight of the composition.

The composition according to the invention can be formulated so as to be suitable for oral administration, topical administration to the skin, or administration by intraepidermal and/or intradermal and/or transdermal and/or subcutaneous injection, and/or microinjection.

The composition according to the present invention for topical administration can be in the form of aqueous or aqueous-alcoholic solutions, oil-in-water (O/W), water-in-oil (W/O) or multiple (for example triple O/W/O or W/O/W) emulsions, nanoemulsions, aqueous gels or dispersions of a fatty phase in an aqueous phase. It can be formulated in the form of a more or less fluid cream, a gel, a hydrogel, a film-forming product (in particular based on high-molecular weight hyaluronic acid which has the property of taking up water and of forming a gel upon spreading), a lotion, a mask, a milk, an oil, a salve, a wax, a foam, a paste, a serum, an ointment, an aerosol, a stick, a soap or a shampoo.

The composition suitable for topical administration can be used in combination with mechanical elements such as palpating-rolling devices having a mechanical and massaging action which causes the product to penetrate and which activates the circulation of the product, or (light, low-frequency, infrared-frequency, etc.) wave-emitting systems which make it possible to activate the response of the skin or to directly increase the effect of the product.

The composition according to the present invention for oral administration can be in the form of a caplet, a pill, a gel capsule, a syrup or a tablet.

The composition according to the present invention for injectable administration is preferably formulated in a sterile form. It can also be in the form of a powder, the solvent being added extemporaneously at the time of use.

The constituents of the composition and also their proportions can be easily chosen by those skilled in the art on the basis of their general knowledge.

The composition can also be included in a device suitable for the mode of administration under consideration.

Such devices can be suitable for topical administration. Mention may in particular be made of patches, occlusive dressings, mini-occlusion chambers, etc. The term "patch" is intended to mean any type of patch known to those skilled in the art, and in particular those which generate a slight current at the level of the skin when stuck to said skin, making it possible to promote the penetration of the product into said skin. The term "mini-occlusion chambers" is intended to mean a device of the small bag type which sticks to the skin, which is filled with the composition and which makes it possible to maintain a significant amount of this composition in contact with the skin so as to increase the amount of product that would diffuse into said skin.

Other devices will be suitable for an injection, in particular suitable for an intraepidermal and/or intradermal and/or transdermal and/or subcutaneous injection and/or a microinjection. Such devices can comprise a needle, microneedles or a needleless injection device. Such devices are well known in mesotherapy.

The invention relates to kits comprising the composition according to the present invention and a syringe or an injector device.

The compounds of general formula (I) of the present invention can be prepared according to the synthesis route as described below or such as they emerge from the various preparation examples given hereinafter in a non-limiting manner.

The general synthesis route for the preparation of the compounds of formula (I) is illustrated in scheme 1 (FIG. 1). The synthesis of the arylthiol derivatives 4 can be carried out by reacting the arenes 1 with chlorosulphonic acid so as to give the corresponding chlorosulphonic arenes 2 which are then reduced with a reducing agent such as zinc powder in the presence of hydrochloric acid, for example so as to give the disulphides of general formula 3. These disulphides are then reduced, for example, by reaction with triphenylphosphine in a dioxanewater medium so as to give the thiols of general formula 4.

The derivatives of general formula 4 can be added to the vinyl derivatives of general formula 5 (commercial or synthesized via the methods known to those skilled in the art) in an aqueous medium, for example water (Synlett, 2007, 925-928) so as to give the derivatives of general formula 6.

The sulphides of general formula 6 can then be oxidized to their corresponding sulphone of general formula 7 via the action of an oxidizing agent such as potassium hydrogen persulphate (oxone®) for example. The compounds of general formula I which are the subject of the present invention are obtained by saponification, using a base such as lithium hydroxide for example, of the esters of general formula 7 in a solvent such as THF, ethanol or water or else in a mixture of these solvents. By way of illustration, it was possible to prepare the following compounds which correspond to general formula (I) of the present invention by following one of the schemes presented above.

EXAMPLES

Example 1

4-[2-(5,5,8,8-tetramethyl-5,6,7,8-tetrahydronaphthalene-2-sulphonyl)ethyl]benzoic acid 5,5,8,8-Tetramethyl-5,6,7,8-tetrahydronaphthalene-2-disulphide

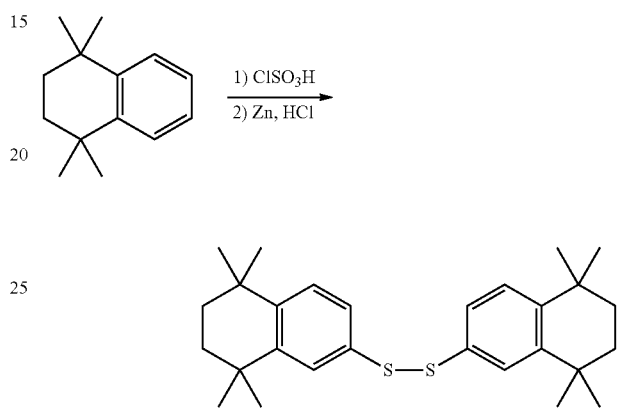

100 g (0.532 mol) of 1,1,4,4-tetramethyl-1,2,3,4-tetrahydronaphthalene are added dropwise to 166.5 ml of chlorosulphonic acid at 0° C., the reaction medium is stirred for 3 h at AT. The mixture is poured onto ice and extracted with ethyl acetate and then the solvent is evaporated off under vacuum. 143 g of brown solid are obtained. This solid is taken up with 660 ml of ethanol, cooled to 0° C., and then 156.6 g of zinc powder are added along with 660 ml of 37% hydrochloric acid. The reaction mixture is stirred overnight at AT and then filtered over celite. The solid plus the celite are taken up with ethyl acetate and then the ethyl acetate phase is washed with NaHCO$_3$. The solvent is evaporated off so as to give 110 g of a brown solid. This solid is crystallized from an ethyl etherethanol mixture so as to give 64 g of 5,5,8,8-tetramethyl-5,6,7,8-tetrahydronaphthalene-2-disulphide in the form of beige solid.

Yield=27%.

5,5,8,8-Tetramethyl-5,6,7,8-tetrahydronaphthalene-2-thiol

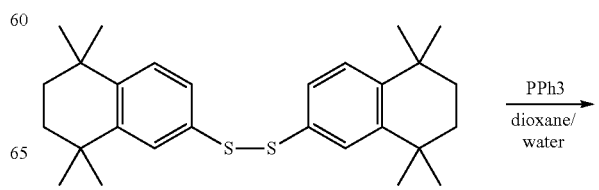

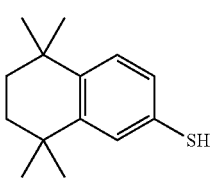

27 g (62.7 mmol) of preceding 5,5,8,8-tetramethyl-5,6,7,8-tetrahydronaphthalene-2-disulphide are suspended in 240 ml of a 91 dioxanewater mixture, then 16.3 g (63 mmol) of triphenylphosphine are added and then the mixture is brought to reflux for 6 hours and then concentrated to dryness. The residue is filtered off over silica (8/2 DCM/hept) so as to give 28 g of 5,5,8,8-tetramethyl-5,6,7,8-tetrahydronaphthalene-2-thiol in the form of a yellow solid.

Yield=100%.

Methyl 4-[2-(5,5,8,8-tetramethyl-5,6,7,8-tetrahydronaphthalen-2-ylsulphanyl)ethyl]benzoate

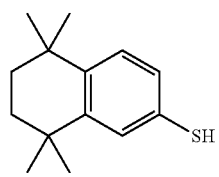

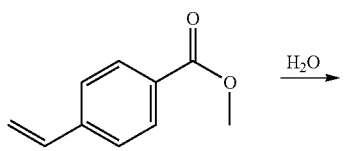

Under nitrogen, a mixture of methyl 4-vinylbenzoate (1.6 g, 9.87 mmol) and 5,5,8,8-tetramethyl-5,6,7,8-tetrahydronaphthalene-2-thiol (2.39 g, 10.85 mmol) in suspension in 15 ml of degassed water is stirred at ambient temperature for 24 hours. The reaction medium is taken up with ethyl acetate and water. After extraction, the organic phase is washed with a 1N sodium hydroxide solution and then a saturated NaCl solution, dried over $MgSO_4$ then concentrated. The compound obtained is chromatographed on a silica gel cartridge (97/3 heptaneethyl acetate). m=2.74 g of methyl 4-[2-(5,5,8,8-tetramethyl-5,6,7,8-tetrahydronaphthalen-2-ylsulphanyl)ethyl]benzoate are collected in the form of a white solid.

Yield=74%.

$^1$H NMR/DMSO, 400 MHz: 1.21; (s, 6H); 1.22; (s, 6H); 1.62; (s, 4H); 2.93 (t, j=7.6 Hz, 2H); 3.24; (t, j=7.6 Hz, 2H); 3.84; (s, 3H); 7.10; (dd, j=8.3 Hz-j=2.0 Hz, 1H); 7.22; (d, j=2.0 Hz, 1H); 7.26; (d, j=8.3 Hz, 1H); 7.39; (d, j=8.3 Hz, 2H); 7.88; (d, j=8.2 Hz, 2H).

Methyl 4-[2-(5,5,8,8-tetramethyl-5,6,7,8-tetrahydronaphthalene-2-sulphonyl)ethyl]benzoate (Compound 4)

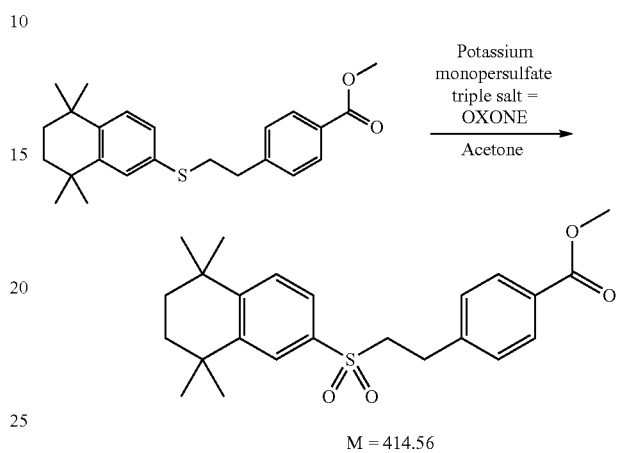

Potassium monopersulphate triple salt (Oxone®) (16.73 g, 27.21 mmol) is added to methyl 4-[2-(5,5,8,8-tetramethyl-5,6,7,8-tetrahydronaphthalen-2-ylsulphanyl)ethyl]benzoate (3.47 g, 9.07 mmol) in solution in 136 ml of acetone. The reaction mixture is stirred overnight at ambient temperature. The medium is filtered and concentrated so as to give 3.54 g of methyl 4-[2-(5,5,8,8-tetramethyl-5,6,7,8-tetrahydronaphthalene-2-sulphonyl)-ethyl]benzoate in the form of a beige solid.

Yield=94%.

$^1$H NMRDMSO, 400 MHz: 1.24 (s, 6H); 1.25; (s, 6H); 1.64; (s, 4H); 3.01; (t, j=7.8 Hz, 2H); 3.74; (t, j=7.5 Hz, 2H); 3.81; (s, 3H); 7.30; (d, j=8.3 Hz, 2H); 7.52; (d, j=8.4 Hz, 1H); 7.57; (dd, j=8.4 Hz-j=1.90 Hz, 1H); 7.74-7.77; (m, 3H).

4-[2-(5,5,8,8-Tetramethyl-5,6,7,8-tetrahydronaphthalene-2-sulphonyl)ethyl]benzoic acid (Compound 1)

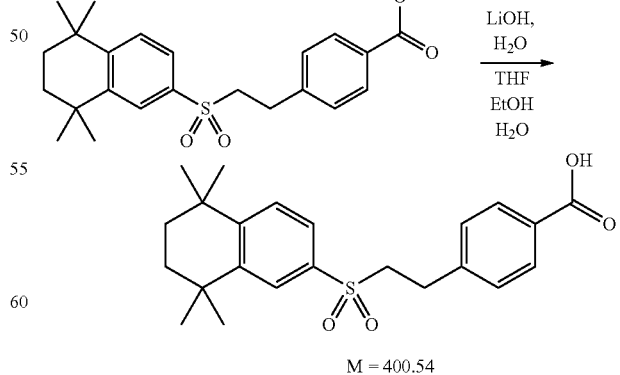

The methyl 4-[2-(5,5,8,8-tetramethyl-5,6,7,8-tetrahydronaphthalene-2-sulphonyl)-ethyl]benzoate (3.54, 8.54 mmol) is placed in solution in 256 ml of tetrahydrofuran, 25.6 ml of ethanol and 12.8 ml of water in a round-bottomed flask. 3.54 g of lithia monohydrate are added. The whole mixture is stirred for 4 hours at reflux. Ambient the reaction medium is concentrated by half, taken up with ethyl acetate and water and then brought to pH6 with 2N HCl. After extraction, the organic phase is washed with a saturated NaCl solution, dried over MgSO$_4$, concentrated and washed with ether. 3 g of 4-[2-(5,5,8,8-tetramethyl-5,6,7,8-tetrahydronaphthalene-2-sulphonyl)ethyl]benzoic acid are obtained in the form of a white solid.

Yield=88%, Mp 203° C.

$^1$H NMR/DMSO, 400 MHz: 1.24; (s, 6H); 1.25; (s, 6H); 1.64; (s, 4H); 2.99; (t, j=7.9 Hz, 2H); 3.72; (t, j=7.5 Hz, 2H); 7.26; (d, j=8.1 Hz, 2H); 7.52-7.60; (m, 2H); 7.74-7.76; (m, 3H); 12.85; (s, 1H).

$^{13}$C NMR/DMSO, 400 MHz: 28.12; (CH$_2$); 31.18; (CH$_3$); 31.26; (CH$_3$); 33.99; (CH$_2$); 34.06; (CH$_2$); 34.23; (C); 34.38; (C); 54.45; (CH$_2$); 124.52; (CH); 125.65; (CH); 127.67; (2CH); 128.57; (CH); 128.93; (C); 129.23; (2CH); 136.33; (C); 142.88; (C); 145.67; (C); 150.59; (C); 167.09; (C).

Example 2

4-[2-(5,5,8,8-tetramethyl-5,6,7,8-tetrahydronaphtha-lene-2-sulphonyl)ethyl]-3-trifluoromethylbenzoic acid In a manner analogous to Example 1 but using 3-trifluo-romethyl-4-vinylbenzoic acid, 4-[2-(5,5,8,8-tetramethyl-5,6,7,8-tetrahydronaphthalene-2-sulphonyl)ethyl]-3-trifluorom-ethylbenzoic acid is obtained.

$^1$H NMR/CDCl$_3$, 400 MHz: 1.24; (s, 6H); 1.25; (s, 6H); 1.66; (s, 4H); 3.17-3.21; (m, 2H); 3.23-3.28; (m, 2H); 7.39; (d, j=8.1 Hz, 1H); 7.44; (d, j=8.4 Hz, 1H); 7.57; (dd, j=8.3 Hz-j=2.0 Hz, 1H); 7.78; (d, j=2.0 Hz, 1H); 8.12; (dd, j=8.0 Hz-j=3.6 Hz, 1H); 8.26; (d, j=1.2 Hz, 1H).

$^{13}$C NMR/CDCl$_3$, 400 MHz: 26.37; (CH$_2$); 29.71; (C); 31.60; (CH$_3$); 31.67; (CH$_3$); 34.53; (CH$_2$); 34.607; (CH$_2$); 34.71; (C); 34.86; (C); 56.76; (CH$_2$); 122.19; (C); 124.84; (CH); 124.91; (C); 126.60; (CH$_2$); 127.98; (CH); 128.27; (CH); 128.33; (CH); 128.39; (C); 128.57; (CH); 129.31; (CF$_3$); 131.83; (CH); 133.69; (C); 135.21; (C); 142.53; (C); 146.84; (C); 151.99; (C); 169.55; (C).

Example 3

4-[2-(3,5,5,8,8-pentamethyl-5,6,7,8-tetrahydronaph-thalene-2-sulphonyl)ethyl]-3-trifluoromethylbenzoic acid In a manner analogous to Example 1 but using 1,1,4,4,6-pentamethyl-1,2,3,4-tetrahydronaphthalene and 3-trifluo-romethyl-4-vinylbenzoic acid, 4-[2-(3,5,5,8,8-pentamethyl-5,6,7,8-tetrahydronaphthalene-2-sulphonyl)ethyl]-3-trifluoromethylbenzoic acid is obtained.

$^1$H NMRCDCl$_3$, 400 MHz: 1.22; (s, 6H); 1.23; (s, 6H); 1.63; (s, 4H); 2.53; (s, 3H); 3.17-3.22; (m, 2H); 3.25-3.30; (m, 2H); 7.18; (d, j=9.7 Hz, 1H); 7.40; (d, j=7.4 Hz, 1H); 7.87; (s, 1H); 8.12; (dd, j=8.0Hz-j=1.4 Hz, 1H); 8.27; (d, j=1.2 Hz, 1H).

$^{13}$C NMRCDCl$_3$, 400 MHz: 19.94; (CH$_3$); 26.07; (CH$_2$); 29.71; (CH$_2$); 31.50; (CH$_3$); 31.61; (CH$_3$); 34.25; (C); 34.53; (C); 34.64; (CH$_2$); 34.67; (CH$_2$); 55.81; (CH$_2$); 128.28; (CH); 128.34; (CH$_2$); 128.96; (CH); 129.35; (CF$_3$); 131.19; (CH); 131.88; (CH); 133.43; (C); 133.68; (CH); 134.14; (C); 142.73; (C); 144.00; (C); 15180; (C); 169.39; (C).

Example 4

Measurement of the Inhibitory Activity on the Isoforms of the CYP26 Enzyme

A cell test using HeLa cells overexpressing either the human CYP26A1 enzyme or the human CYP26B1 enzyme, similar to that described in White et al.(Proc Natl Acad Sci U S A. 2000 Jun 6; 97(12): 6403-8), was used. Briefly, the cells were plated out in multiple-well plates and treated with the compounds according to the invention or the positive controls such as liarozole or rambazole, and subsequently exposed to radiolabelled retinoic acid (3H-RA). After the incubation time of 3 h, the reaction was stopped and an extraction phase was carried out in order to separate the aqueous and organic layers. The amount of radioactivity present in the aqueous layer was then measured as an indicator of the amount of RA which was metabolized.

A first experiment using 3 different concentrations of compounds according to the invention (0.1, 1 and 10 μM) was carried out in order to evaluate the inhibitory activity of the compounds. A second test was then carried out with a wide range of concentrations (0.01, 0.1, 0.5, 1, 5 and 10 μM). The results obtained during these two tests are similar.

The following table lists the mean of the AC50 values obtained over these two experiments.

| Mean AC50 (μM) | Liarozole | Rambazole | Example 1 according to the invention |
|---|---|---|---|
| CYP26A1 | 4.00 | 0.004 | 0.19 |
| CYP26B1 | 0.32 | 0.064 | 50.33 |
| CYP26B1/CYP26A1 | 0.08 | 16.82 | 261.50 |
| CYP26A1/CYP26B1 specificity | − | + | +++ |

Rambazole is active on the inhibition of the activity of the two isoforms of the enzyme.

As regards Liarozole, it is more active on CYP26B1 than on CYP26A1.

The compounds according to the invention exhibit a CYP26B1CYP26A1 selectivity ratio of greater than 260, with a very strong activity on the CYP26A1 isoform, of about 0.1 μM, and an extremely weak, or even negligible, activity on the CYP26B 1 isoform, of about 50 μM.

These results clearly demonstrate that the compounds according to the invention act as a RAMBA with direct action on CYP26. The compounds according to the invention demonstrate great selectivity for the CYP26A1 isoform compared with the CYP26B1 isoform.

Example 5

Measurement of the Thickness of the Stratum Corneum in Fuzzy rats

Male Fuzzy rats are separated into four batches each comprising five rats. A topical treatment is carried out on each batch by administering, respectively, a carrier acting as a control, a dose of 0.000001% of retinol, a dose of 0.1% of retinol and a dose of 0.3% of a compound according to the invention corresponding to Example 1.

24 days after the treatment, the rats are euthanized and a 10 μm section of skin is sampled in order to perform a biopsy. A 1M NaOH solution is added to each section in order to soften the stratum corneum. The photos under a microscope are taken in a time period of 2 minutes after the addition of the 1M NaOH solution.

The table below presents the results on the thickness of the stratum corneum for the various batches.

|  | Thickness of the stratum corneum (μm) | Thickness of the stratum corneum relative to the carrier |
|---|---|---|
| Carrier | 42.59 | 1 |
| 0.3% Compound 1 | 24.07 | 0.57 |
| 0.000001% Retinol | 41.60 | 0.98 |
| 0.1% Retinol | 26.24 | 0.62 |

A stratum corneum thickness of 41.60 μm is measured in the rats treated with 0.000001% of retinol. This thickness is approximately equivalent to that of the control batch that would have received a simple carrier (42.59 μm).

A decrease in the thickness of the stratum corneum in the rats treated with 0.1% of retinol (0.62) and in the rats treated with Compound 1 of the invention (0.57) is observed.

The decrease in the thickness of the stratum corneum is even slightly greater with Compound 1, compared with 0.1% of retinol serving as a reference.

Figure 2:
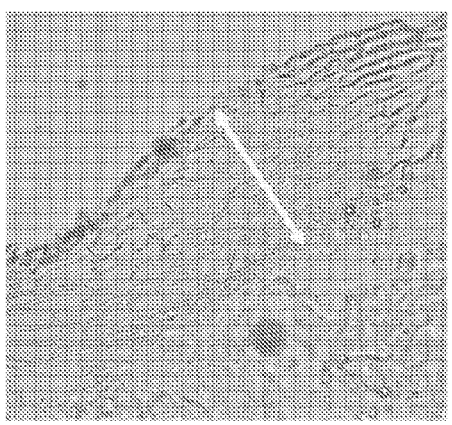
FIG. 2: Photograph of the stratum corneum in a rat treated with a carrier.
Figure 3:
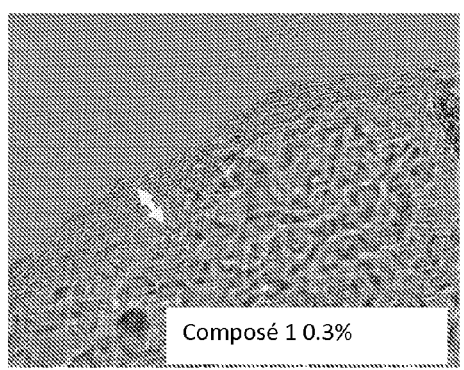
FIG. 3: Photograph of the stratum corneum in a rat treated with compound 1 of the invention.

The results are also illustrated by FIGS. 2 and 3 which represent photographs of the keratinous layer in the rats having received the carrier and in the rats treated with 0.3% of Compound 1 of the invention. The photographs clearly show the decrease in the thickness of the stratum corneum for the rats treated with 0.3% of Compound 1 of the invention.

These results clearly demonstrate that the compounds according to the invention thus make it possible to decrease the thickness of the stratum corneum and can therefore be used in treatments, in particular by slimming down the skin, more particularly against skin ageing, acne by decreasing keratinocyte hyperplasia in the pilosebaceous duct (responsible for microcomedones) and the formation of acne lesions, but also ichthyosis by elimination of all the hyperplastic and hyperkeratinized areas.

The invention claimed is:

1. A compound or a salt thereof of general formula (I) below:

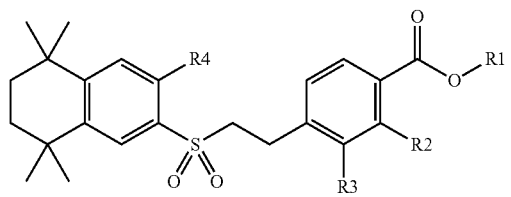

(I)

in which:
R1 represents a hydrogen atom or a $C_1$-$C_3$ alkyl;
R2 represents a hydrogen, a $C_1$-$C_3$ alkyl, a fluorine, or a $CF_3$ radical;
R3 represents a hydrogen, a $C_1$-$C_3$ alkyl, a fluorine, or a $CF_3$ radical; and
R4 represents a $C_1$-$C_3$ alkyl, or a $CF_3$ radical.

2. The compound according to claim 1, wherein:
R1 is selected from the group consisting of a hydrogen, a methyl and an ethyl;
R2 is selected from the group consisting of a hydrogen, a methyl, a fluorine, or a $CF_3$ radical;
R3 is selected from the group consisting of a hydrogen, a methyl, a fluorine, or a $CF_3$ radical; and
R4 is selected from the group consisting of a hydrogen, a methyl, and a $CF_3$ radical.

3. The compound according to claim 1, wherein the compound is selected from the group consisting of:
4-[2-(5,5,8,8-tetramethyl-5,6,7,8-tetrahydronaphthalene-2-sulphonyl)ethyl]benzoic acid;
4-[2-(5,5,8,8-tetramethyl-5,6,7,8-tetrahydronaphthalene-2-sulphonyl)ethyl]-3-trifluoromethylbenzoic acid;
4-[2-(3,5,5,8,8-pentamethyl-5,6,7,8-tetrahydronaphthalene-2-sulphonyl)ethyl]-3-trifluoromethylbenzoic acid;
methyl 4-[2-(5,5,8,8-tetramethyl-5,6,7,8-tetrahydronaphthalene-2-sulphonyl)ethyl]benzoate;
ethyl 4-[2-(5,5,8,8-tetramethyl-5,6,7,8-tetrahydronaphthalene-2-sulphonyl)ethyl]benzoate;
methyl 4-[2-(5,5,8,8-tetramethyl-5,6,7,8-tetrahydronaphthalene-2-sulphonyl)ethyl]-3-trifluoromethyl benzoate;
ethyl 4-[2-(5,5,8,8-tetramethyl-5,6,7,8-tetrahydronaphthalene-2-sulphonyl)ethyl]-3-trifluoromethyl benzoate;
2-methyl-4-[2-(5,5,8,8-tetramethyl-5,6,7,8-tetrahydronaphthalene-2-sulphonyl)ethyl]benzoic acid;
2-fluoro-4-[2-(5,5,8,8-tetramethyl-5,6,7,8-tetrahydronaphthalene-2-sulphonyl)ethyl]benzoic acid;
4-[2-(5,5,8,8-tetramethyl-5,6,7,8-tetrahydronaphthalene-2-sulphonyl)ethyl]-2-trifluoromethyl benzoic acid;
3-methyl-4-[2-(5,5,8,8-tetramethyl-5,6,7,8-tetrahydronaphthalene-2-sulphonyl)ethyl]benzoic acid;
3-fluoro-4-[2-(5,5,8,8-tetramethyl-5,6,7,8-tetrahydronaphthalene-2-sulphonyl)ethyl]benzoic acid;
4-[2-(5,5,8,8-tetramethyl-3-trifluoromethyl-5,6,7,8-tetrahydronaphthalene-2-sulphonyl)ethyl]benzoic acid;
3-methyl-4-[2-(3,5,5,8,8-pentamethyl-5,6,7,8-tetrahydronaphthalene-2-sulphonyl)ethyl]benzoic acid;
2-methyl-4-[2-(3,5,5,8,8-pentamethyl-5,6,7,8-tetrahydronaphthalene-2-sulphonyl)ethyl]benzoic acid;
2,3-dimethyl-4-[2-(5,5,8,8-tetramethyl-5,6,7,8-tetrahydronaphthalene-2-sulphonyl)ethyl]benzoic acid;
2,3-difluoro-4-[2-(5,5,8,8-tetramethyl-5,6,7,8-tetrahydronaphthalene-2-sulphonyl)ethyl]benzoic acid; and
methyl 2-methyl-4-[2-(3,5,5,8,8-pentamethyl-5,6,7,8-tetrahydronaphthalene-2-sulphonyl)ethyl]benzoate.

4. The compound according to claim 1, wherein the compound is selected from the group consisting of:
4-[2-(5,5,8,8-tetramethyl-5,6,7,8-tetrahydronaphthalene-2-sulphonyl)ethyl]benzoic acid;
4-[2-(5,5,8,8-tetramethyl-5,6,7,8-tetrahydronaphthalene-2-sulphonyl)ethyl]-3-trifluoromethylbenzoic acid; and
4-[2-(3,5,5,8,8-pentamethyl-5,6,7,8-tetrahydronaphthalene-2-sulphonyl)ethyl]-3-trifluoromethylbenzoic acid.

5. The compound according to claim 1, wherein the compound is 4-[2-(5,5,8,8-tetramethyl-5,6,7,8-tetrahydronaphthalene-2-sulphonyl)ethyl]benzoic acid.

6. A composition comprising a compound according to claim 1, in combination with a solvent or a support.

7. The composition according to claim 6, 1 wherein the solvent or support is dermatologically acceptable.

8. The compound according to claim 1, wherein the compound is formulated for use as a medicament.

9. A method of treating a pathological condition, the method comprising administering an effective amount of the compound according to claim 1 to an individual subject in need thereof, wherein the pathological condition is selected from:

1) common acne, comedonal acne, polymorphic acne, acne rosacea, nodulocystic acne, acne conglobata, senile acne, solar acne, acne medicamentosa or occupational acne;
2) ichthyosis, ichthyosiform conditions, lamellar ichthyosis, Darier's disease, palmoplantar keratodermia, leukoplakia, pityriasis rubra pilaris and leucoplasiform conditions, or cutaneous or mucosal (buccal) lichen;
3) cutaneous, mucosal or ungueal psoriasis, psoriatic arthritis, atopic dermatitis or various forms of eczema;
4) skin disorders caused by exposure to UV radiation for reducing actinic keratoses and pigmentations;
5) any pathological conditions associated with chronological or actinic ageing;
6) common warts, flat warts, molluscum contagiosum and epidermodysplasia verruciformis, or oral or floride papillomatoses;
7) lupus erythematosus, bullous immune diseases or collagen diseases;
8) stigmata of epidermal and/or dermal atrophy induced by local or systemic corticosteroids, or any other form of cutaneous atrophy;
9) healing disorders, treating or repairing stretch marks, or promoting healing;
10) tinea pedis or tinea versicolor;
11) hyperpigmentation, melasma, hypopigmentation or vitiligo;
12) actinic keratoses, Bowen's disease, in-situ carcinomas, keratoacanthoma and skin cancers optionally basal cell carcinoma (BCC), squamous cell carcinoma (SCC) and cutaneous lymphomas, acute promyelocytic leukaemia, neuroblastomas, acute myeloid leukaemias, prostate cancer or breast cancer.

10. The method according to claim 9, wherein the pathological condition is selected from the group consisting of acne, ichthyosis, ichthyosiform conditions, palmoplantar hyperkeratosis and psoriasis.

11. A method of treating skin ageing, the method comprising administering an effective amount of the compound of claim 1 to an individual subject in need thereof.

12. The method according to claim 11, for treating cutaneous atrophy, pigmentation spots, skin dryness, skin roughness, solar elastosis or telangiectasia.

13. A cosmetic method comprising administering an effective amount of the compound of claim 1 to an individual subject in need thereof to maintain and/or stimulate the moisture of the skin, to treat dry skin, to treat ageing of the skin or skin appendages and/or photoageing, to treat pigmentation spots or wrinkles, for reducing ptosis, for improving quality and/or transparency of the skin, for improving or restoring suppleness, elasticity and/or tonicity of the skin, or for firming the skin.

14. The composition according to claim 6, wherein the composition comprises a dose ranging from 0.000001% to 10% by total weight of the compound relative to the total weight of the composition.

15. The compound according to claim 2, wherein R1 is a hydrogen.

16. The composition according to claim 14, wherein the dose ranges from 0.001% to 5% by total weight of the compound relative to the total weight of the composition.

17. The composition of claim 15, wherein the dose ranges from 0.1% to 3% by total weight of the compound relative to the total weight of the composition.

18. The method of claim 9, wherein the cutaneous lymphoma is T lymphoma.

\* \* \* \* \*